(12) United States Patent
Chen

(10) Patent No.: US 10,602,990 B2
(45) Date of Patent: Mar. 31, 2020

(54) BLOOD PRESSURE MEASUREMENT APPARATUS AND BLOOD PRESSURE MEASUREMENT METHOD

(71) Applicant: MegaChips Corporation, Osaka-shi (JP)

(72) Inventor: Handa Chen, Osaka (JP)

(73) Assignee: MEGACHIPS CORPORATION, Osaka (JP)

(*) Notice: Subject to any disclaimer, the term of this patent is extended or adjusted under 35 U.S.C. 154(b) by 310 days.

(21) Appl. No.: 15/666,904

(22) Filed: Aug. 2, 2017

(65) Prior Publication Data
US 2017/0325751 A1 Nov. 16, 2017

Related U.S. Application Data

(63) Continuation of application No. PCT/JP2015/084640, filed on Dec. 10, 2015.

(30) Foreign Application Priority Data

Feb. 18, 2015 (JP) ................................ 2015-029390

(51) Int. Cl.
*A61B 5/02* (2006.01)
*A61B 5/00* (2006.01)
(Continued)

(52) U.S. Cl.
CPC ........ *A61B 5/7278* (2013.01); *A61B 5/02108* (2013.01); *A61B 5/7225* (2013.01);
(Continued)

(58) Field of Classification Search
None
See application file for complete search history.

(56) References Cited

U.S. PATENT DOCUMENTS

2009/0326386 A1* 12/2009 Sethi ..................... A61B 5/021
600/480

FOREIGN PATENT DOCUMENTS

JP 10-295657 11/1998
JP 11-155826 6/1999
(Continued)

OTHER PUBLICATIONS

International Search Report dated Mar. 1, 2016 in PCT/JP2015/084640, filed on Dec. 10, 2015.
(Continued)

*Primary Examiner* — Joel F Brutus
(74) *Attorney, Agent, or Firm* — Xsensus, LLP

(57) ABSTRACT

A blood pressure measurement apparatus includes circuitry configured to: detect a pulse of a subject, and obtain a photoplethysmography signal; and obtain estimated blood pressure of the subject based on the photoplethysmography signal. The circuitry receives parameter information, generates time information based on the photoplethysmography signal, applies a blood pressure estimation equation to the time information and the parameter information to calculate the estimated blood pressure, receives basic blood pressure information for the subject and the time information, and performs learning processing of applying a learning operational equation to statistical time information, which is obtained by performing statistical processing on the time information, and the basic blood pressure information to update the parameter information.

5 Claims, 4 Drawing Sheets

(51) Int. Cl.
*A61B 5/021* (2006.01)
*A61B 5/024* (2006.01)
(52) U.S. Cl.
CPC ............ *A61B 5/7235* (2013.01); *A61B 5/742* (2013.01); *A61B 5/02416* (2013.01)

(56) References Cited

FOREIGN PATENT DOCUMENTS

JP 2001-137203 5/2001
WO WO 2015/098977 A1 7/2015

OTHER PUBLICATIONS

Japanese Office Action dated Sep. 18, 2018 in Japanese Application No. 2015-029390.

* cited by examiner

F I G. 1
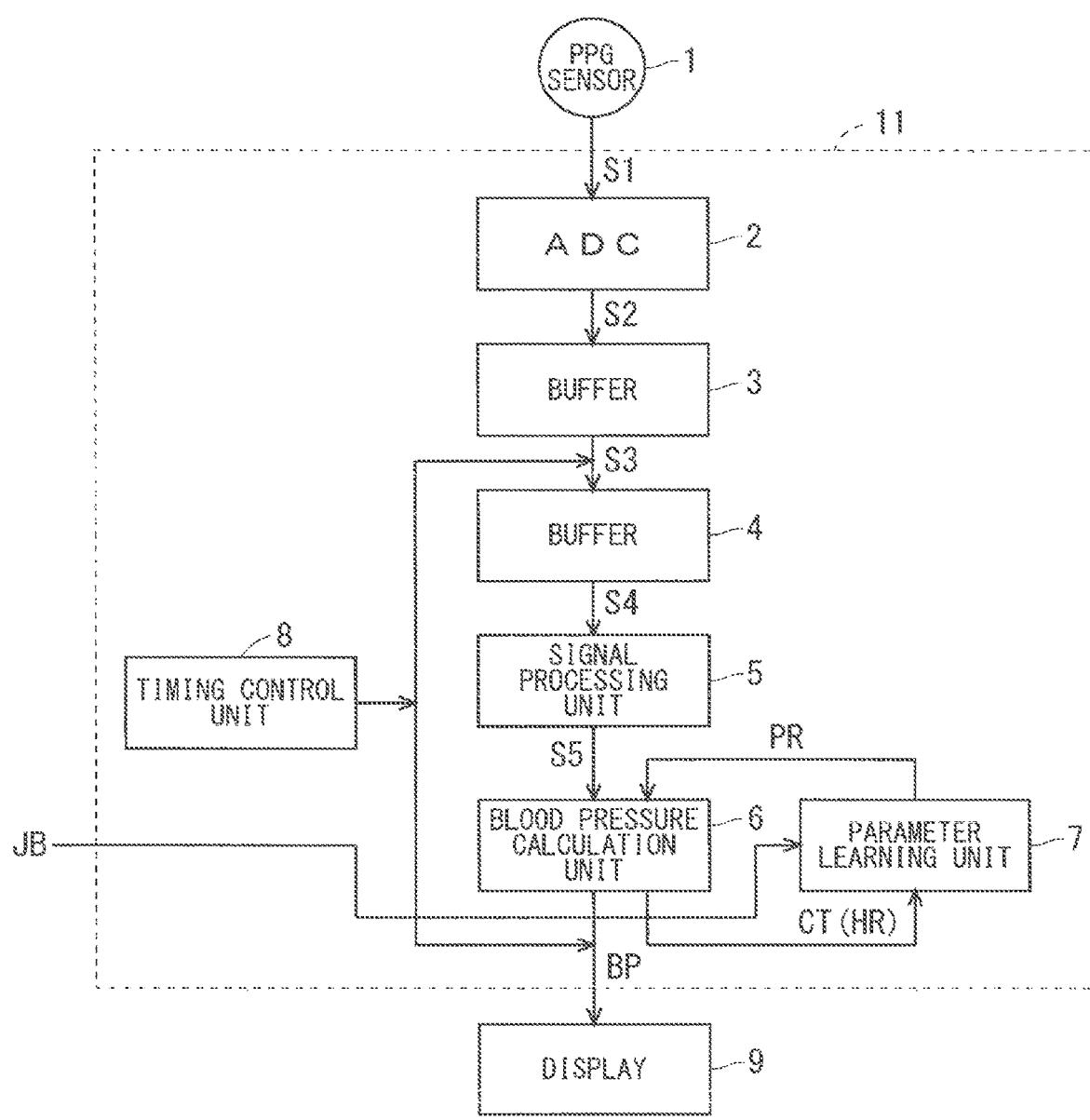

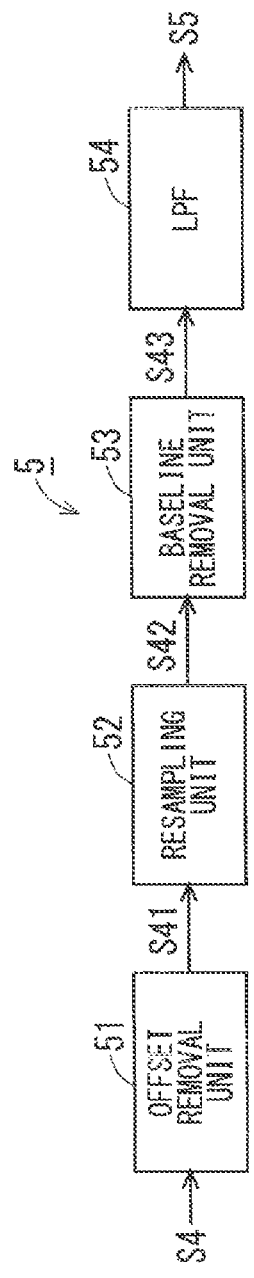
F I G. 2A
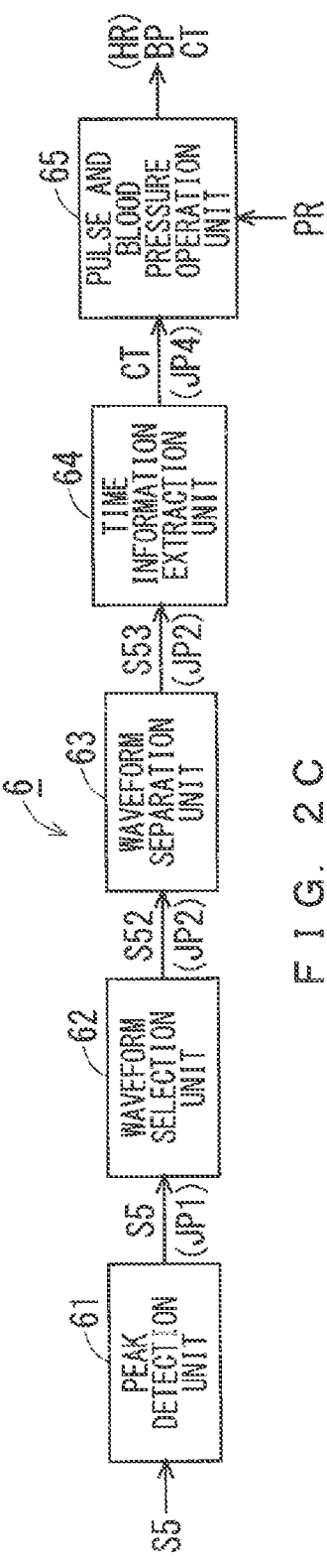
F I G. 2B
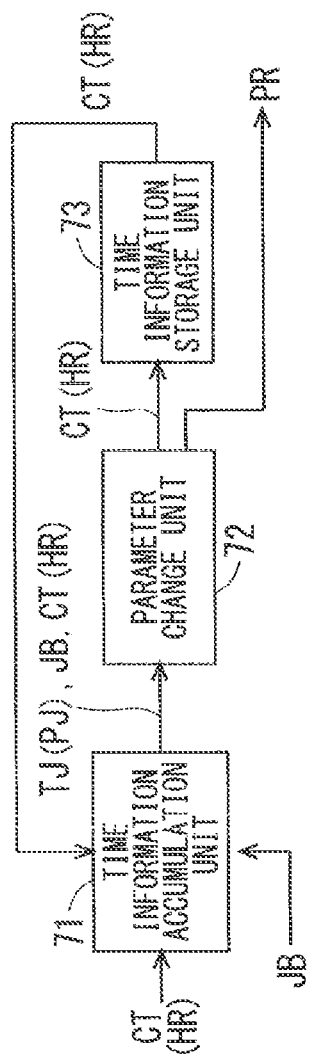
F I G. 2C

BLOOD PRESSURE MEASUREMENT APPARATUS AND BLOOD PRESSURE MEASUREMENT METHOD

BACKGROUND OF THE INVENTION

Field of the Invention

The present invention relates to blood pressure measurement apparatuses and blood pressure measurement methods, and in particular, to a blood pressure measurement apparatus using photoplethysmography signals obtained by a photoplethysmography sensor.

Description of the Background Art

Progress has recently been made in developing watch-like wearable healthcare products including photoplethysmography sensors. A photoplethysmography sensor can shine light from a light emitting device onto the arm, the finger, and the like, detect reflected or transmitted light using a light receiving device, and convert a light receiving signal into an electric signal to obtain a photoplethysmography signal (photoelectric pulse wave signal), and a pulse measured based on the photoplethysmography signal is displayed by an LCD and the like. Such a photoelectric pulse watch already exists on the market, but the number of wearable photoelectric sphygmomanometers is still small.

In blood pressure measurement technology, a cuff auscultatory method (using Korotkoff sounds) and a cuff oscillometric method are both known as a conventional method of noninvasively measuring blood pressure. The former uses a mercurial sphygmomanometer commonly used in hospitals, and the latter uses a digital automatic sphygmomanometer for home use.

Research has recently been conducted on a method of measuring blood pressure using an electrocardiographic sensor and a photoelectric sensor in combination. The principle is that blood pressure is associated with a pulse transfer time from detection of an R wave of an electrocardiogram (ECG) signal to detection of a first peak of a photoplethysmography (PPG) signal, and is estimated using a linear auto-regressive model. This type of blood pressure measurement algorithm requires the electrocardiogram signal and the photoplethysmography signal to be obtained at the same time, and is thus inconvenient for wearable devices.

To solve the problem, a method of dividing a time of the PPG signal into a systolic upstroke time and a diastolic time, associating the former with systolic blood pressure and the latter with diastolic blood pressure, and estimating blood pressure using the linear auto-regressive model has been proposed. Japanese Patent Application Laid-Open Publication No. 11-155826 discloses technology similar to the above-mentioned method.

SUMMARY

A blood pressure measurement apparatus includes circuitry configured to: detect a pulse of a subject to obtain a photoplethysmography signal; and obtain estimated blood pressure of the subject based on the photoplethysmography signal. The circuitry is configured to receive parameter information, generate time information based on the photoplethysmography signal, apply a blood pressure estimation equation to the time information and the parameter information to calculate the estimated blood pressure, receive basic blood pressure information for the subject and the time information, and perform learning processing of applying a learning operational equation to statistical time information, which is obtained by performing statistical processing on the time information, and the basic blood pressure information to update the parameter information.

BRIEF DESCRIPTION OF THE DRAWINGS

FIG. 1 is a block diagram showing the overall configuration of a blood pressure measurement apparatus according to an embodiment of the present invention;

FIGS. 2A, 2B, and 2C are block diagrams respectively showing the internal configuration of a signal processing unit, the internal configuration of a blood pressure calculation unit, and the internal configuration of a parameter learning unit shown in FIG. 1;

DESCRIPTION OF THE PREFERRED EMBODIMENTS

1. Overall Configuration

Figure 3:
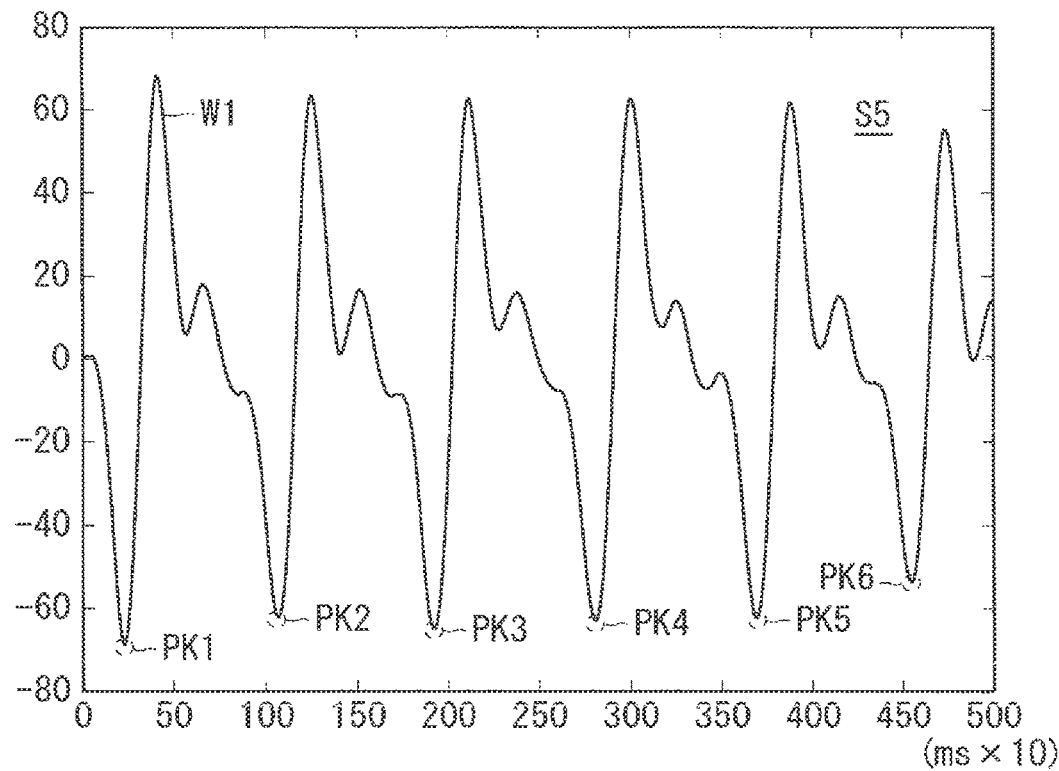
FIG. 3 is a graph showing peak positions detected by a peak detection unit.

FIG. 1 is a block diagram showing the overall configuration of a blood pressure measurement apparatus according to an embodiment of the present invention. As shown in FIG. 1, the blood pressure measurement apparatus according to the present embodiment includes a PPG sensor 1 that is a photoplethysmography sensor, a blood pressure measurement unit 11, and a display 9.

The PPG sensor 1 shines light from a light emitting device onto the arm, the finger, and the like, detects reflected or transmitted light using a light receiving device, converts a light receiving signal into an electric signal to detect a pulse, and outputs a photoplethysmography signal (PPG signal) S1 to the blood pressure measurement unit 11. The PPG sensor 1 samples the photoplethysmography signal S1 at a sampling frequency of approximately 100 Hz to 300 Hz.

The blood pressure measurement unit 11 measures estimated blood pressure indicating maximum blood pressure (systolic blood pressure value) and minimum blood pressure (diastolic blood pressure value) using a blood pressure estimation equation based on the photoplethysmography signal S1, and outputs blood pressure information BP indicating the estimated blood pressure. The display 9 displays the estimated blood pressure indicated by the blood pressure information BP so that the estimated blood pressure can visually be recognized.

The blood pressure measurement apparatus having such configuration can be achieved, for example, as a wristwatch-like compact wearable apparatus obtained by providing the function of the blood pressure measurement unit 11 to an operation unit equipped with the PPG sensor 1 and the display 9, being wearable on the arm and the like, and incorporating therein a CPU and the like.

2. Blood Pressure Measurement Unit

The blood pressure measurement unit 11 includes an ADC 2, a buffer 3, a buffer 4, a signal processing unit 5, a blood pressure calculation unit 6, a parameter learning unit 7, and a timing control unit 8. In achieving the wearable blood pressure measurement apparatus, at least some of the above-mentioned units 2 to 8 of the blood pressure measurement unit 11 are executed by program processing using a CPU based on software.

The ADC 2 performs A/D conversion on the photoplethysmography signal S1, and outputs a digitized pulse signal S2 to the buffer 3. The buffer 3 buffers the pulse signal S2 at an interval of 30 sec to 60 sec, and outputs a pulse signal S3. The buffer 4 buffers the pulse signal S3 at an interval of 3 sec to 5 sec, and outputs a pulse signal S4 to the signal processing unit 5. The signal processing unit 5 performs various types of signal processing on the pulse signal S4, and outputs a pulse signal S5 to the blood pressure calculation unit 6.

The blood pressure calculation unit 6 calculates time information CT based on the pulse signal S5, and applies received parameter information PR and the time information CT to the blood pressure estimation equation described later to calculate the estimated blood pressure. This means that the blood pressure calculation unit 6 calculates the estimated blood pressure in units of the pulse signal S4 obtained through buffering by the buffer 4 (at an interval of 3 sec to 5 sec).

The blood pressure calculation unit 6 outputs the blood pressure information BP indicating the estimated blood pressure to the display 9, and outputs the time information CT to the parameter learning unit 7. The blood pressure calculation unit 6 has a pulse measurement function of measuring a pulse based on the pulse signal S5 to further calculate a measured pulse, and outputting pulse information HR indicating the measured pulse to the parameter learning unit 7.

The parameter learning unit 7 performs statistical processing on the time information CT to obtain statistical time information TJ. The parameter learning unit 7 then applies the statistical time information TJ and basic blood pressure information JB, which is described later, to a learning operational equation to update the parameter information PR, and outputs the updated parameter information PR to the blood pressure calculation unit 6.

The blood pressure calculation unit 6 outputs the pulse information HR as necessary by using the pulse measurement function, and the parameter learning unit 7 performs statistical processing on the pulse information HR as necessary to obtain statistical pulse information PJ, and applies the statistical time information TJ and the basic blood pressure information JB as well as the statistical pulse information PJ to the learning operational equation to obtain the parameter information PR.

The timing control unit 8 controls a timing at which the buffer 3 outputs the pulse signal S3, a timing at which the blood pressure calculation unit 6 outputs the blood pressure information BP, and the like.

(2-1. Signal Processing Unit)

FIGS. 2A, 2B, and 2C are block diagrams respectively showing the internal configuration of the signal processing unit 5, the internal configuration of the blood pressure calculation unit 6, and the internal configuration of the parameter learning unit 7 shown in FIG. 1. FIG. 2A shows the internal configuration of the signal processing unit 5, FIG. 2B shows the internal configuration of the blood pressure calculation unit 6, and FIG. 2C shows the internal configuration of the parameter learning unit 7.

The internal configuration of the signal processing unit 5 is described first with reference to FIG. 2A. The signal processing unit 5 includes an offset removal unit 51, a resampling unit 52, a baseline removal unit 53, and a low-pass filter (LPF) 54.

The offset removal unit 51 performs offset removal processing so that an initial input level of the pulse signal S4 is "0", and outputs a pulse signal S41 obtained after offset removal to the resampling unit 52. The resampling unit 52 performs resampling processing so that the pulse signal S41 has a data rate suitable for blood pressure and pulse calculation, and outputs a pulse signal S42. The baseline removal unit 53 removes a signal wave as a baseline from the pulse signal S42, and outputs a pulse signal S43 to the LPF 54. The LPF 54 performs filtering processing of removing a component with frequency higher than cutoff frequency on the pulse signal S43, and outputs the pulse signal S5.

(2-2. Blood Pressure Calculation Unit)

The internal configuration of the blood pressure calculation unit 6 is described next with reference to FIG. 2B. The blood pressure calculation unit 6 includes a peak detection unit 61, a waveform selection unit 62, a waveform separation unit 63, a time information extraction unit 64, and a pulse and blood pressure operation unit 65.

Figure 4:
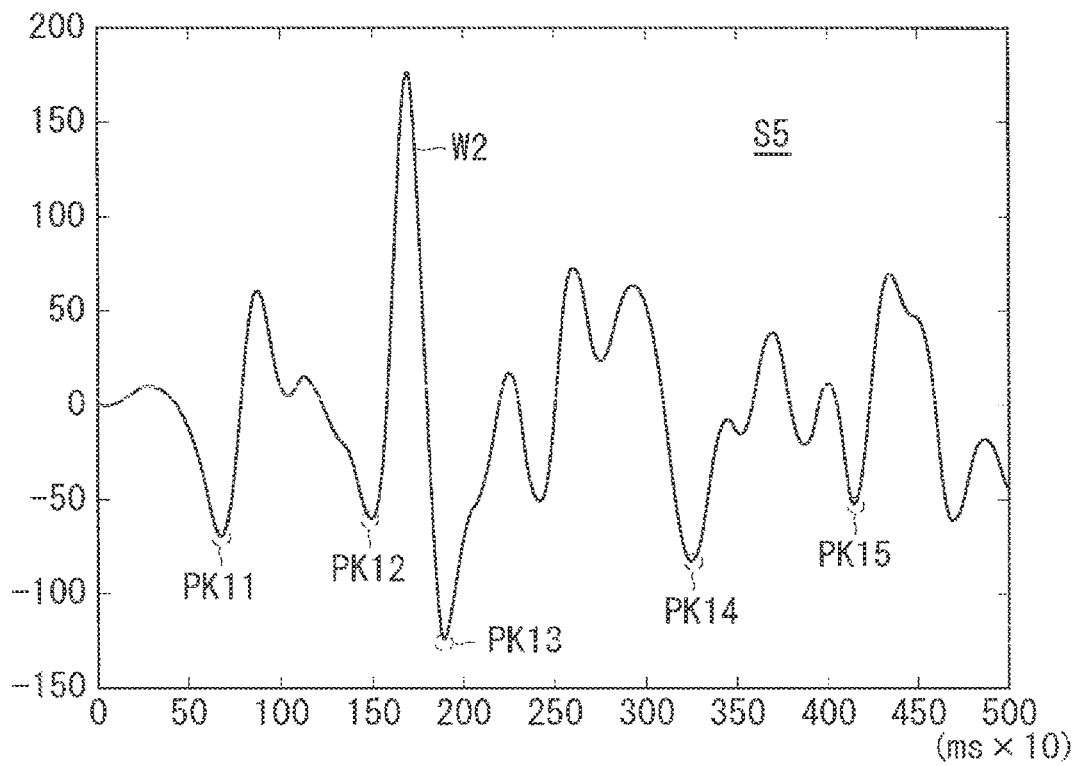
FIG. 4 is a graph showing peak positions detected by the peak detection unit.

The peak detection unit 61 detects a peak position PK indicating a maximum or minimum value of the pulse signal S5. FIGS. 3 and 4 are graphs each showing peak positions PK detected by the peak detection unit 61. The horizontal axis of each of FIGS. 3 and 4 indicates the number of samples in milliseconds (ms)×10 to correspond to a sampling frequency of the photoplethysmography signal S1 of 100 Hz. On the other hand, the vertical axis of each of FIGS. 3 and 4 indicates spectral intensity. The spectral intensity is indicated as relative spectral intensity.

In a case where the pulse signal S5 as obtained has a detected waveform W1 shown in FIG. 3, the peak detection unit 61 detects peak positions PK1 to PK6 in a negative direction, for example. Peak information JP1 including information indicating spectral intensities and times of the respective peak positions PK1 to PK6 as well as the pulse signal S5 are output to the waveform selection unit 62. Similarly, in a case where the pulse signal S5 as obtained has a detected waveform W2 shown in FIG. 4, the peak detection unit 61 detects peak positions PK11 to PK15 in the negative direction, for example.

The waveform selection unit 62 determines whether the waveform is a normal waveform from a variation of time distances between peak positions PKi (differential times between adjacent peak positions PKi(PK1$i$), PK(i+1), and (PK1($i$+1)); hereinafter referred to as "peak-to-peak distances"), and discards an abnormal waveform.

For example, the detected waveform W1 shown in FIG. 3 is determined to be a normal waveform as a variation of the peak-to-peak distances between the peak positions PK1 to PK6 is small, whereas the detected waveform W2 shown in FIG. 4 is determined to be an abnormal waveform as a variation of the peak-to-peak distances between the peak positions PK11 to PK15 is large.

Furthermore, if a mean value of the peak-to-peak distances of a waveform of the pulse signal S5 determined to be a normal waveform without being discarded is within an allowable range, the mean value is determined as a value of the normal waveform that can be used to calculate the measured pulse p, and, if the mean value is out of the allowable range, the mean value is discarded without being used in the subsequent processing. An allowable minimum value and an allowable maximum value are usually set to define the allowable range, and the mean value is within the allowable range when the mean value is equal to or greater than the allowable minimum value and is equal to or smaller than the allowable maximum value.

As described above, the waveform selection unit 62 selects, from the received pulse signal S5, the pulse signal S5 meeting each of a condition (1) that "a variation of the peak-to-peak distances does not indicate the abnormal waveform" and a condition (2) that "the mean value of the peak-to-peak distances is within the allowable range" based on the peak information JP1, and outputs the selected pulse signal S5 to the waveform separation unit 63 as a selected pulse signal S52.

Processing performed by the waveform selection unit 62 in line with the above-mentioned conditions (1) and (2) is specifically described below. Peak positions PK of five seconds of the pulse signal S5 obtained through buffering by the buffer 4 are detected, and the peak-to-peak distances are calculated. Assume that peak-to-peak distances {t1, t2, t3, t4, t5} are obtained, for example. If a variation difference between maximum values t_max=max(t1, t2, t3, t4, t5) and minimum values t_min=min (t1, t2, t3, t4, t5) is equal to or greater than 20 samples (corresponding to 200 ms in a case where the photoplethysmography signal S1 is sampled at 100 Hz), the waveform is discarded as the abnormal waveform not meeting the condition (1). This means that, if the above-mentioned variation difference is equal to or greater than 20 samples, the waveform is determined as the abnormal waveform as the pulse signal S5 obtained based on the photoplethysmography signal S1 has jitter of 0.2 sec or more.

On the other hand, if the variation difference (t_max− t_min) is smaller than 20 samples, the waveform is determined to meet the condition (1). A mean value t_mean of {t1, t2, t3, t4, t5} is obtained when the condition (1) is met, and the pulse signal S5 is determined to meet the condition (2) and is output as the selected pulse signal S52 if the mean value t_mean is within a range of 30 ms×10 to 150 ms×10 (corresponding to 200 beats per minute (bpm) to 40 bpm of a pulse), and is discarded if the condition (2) is not met. As described above, the waveform selection unit 62 imposes a qualifying standard for pulse measurement using the conditions (1) and (2) on the pulse signal S5.

The waveform selection unit 62 outputs the selected pulse signal S52 along with peak information JP2, which is the peak information JP1 corresponding to the selected pulse signal S52.

The waveform separation unit 63 sequentially extracts, from the selected pulse signal S52, one wavelength of single pulse signals S53 defined by the peak-to-peak distances, and outputs the extracted single pulse signals S53. The single pulse signals S53 are output along with the peak information JP2 corresponding to the single pulse signals S53.

The time information extraction unit 64 measures an up time st (a rise time) and a down time dt (a fall time) with respect to each of the single pulse signals S53 as received. The up time st is a transition time during which the single pulse signal S53 of the photoplethysmography signal S1 transitions in a direction in which the single pulse signal S53 rises, and the down time dt is a transition time during which the single pulse signal S53 of the photoelectric pulse signal S1 transitions in a direction in which the single pulse signal S53 falls.

Figure 5:
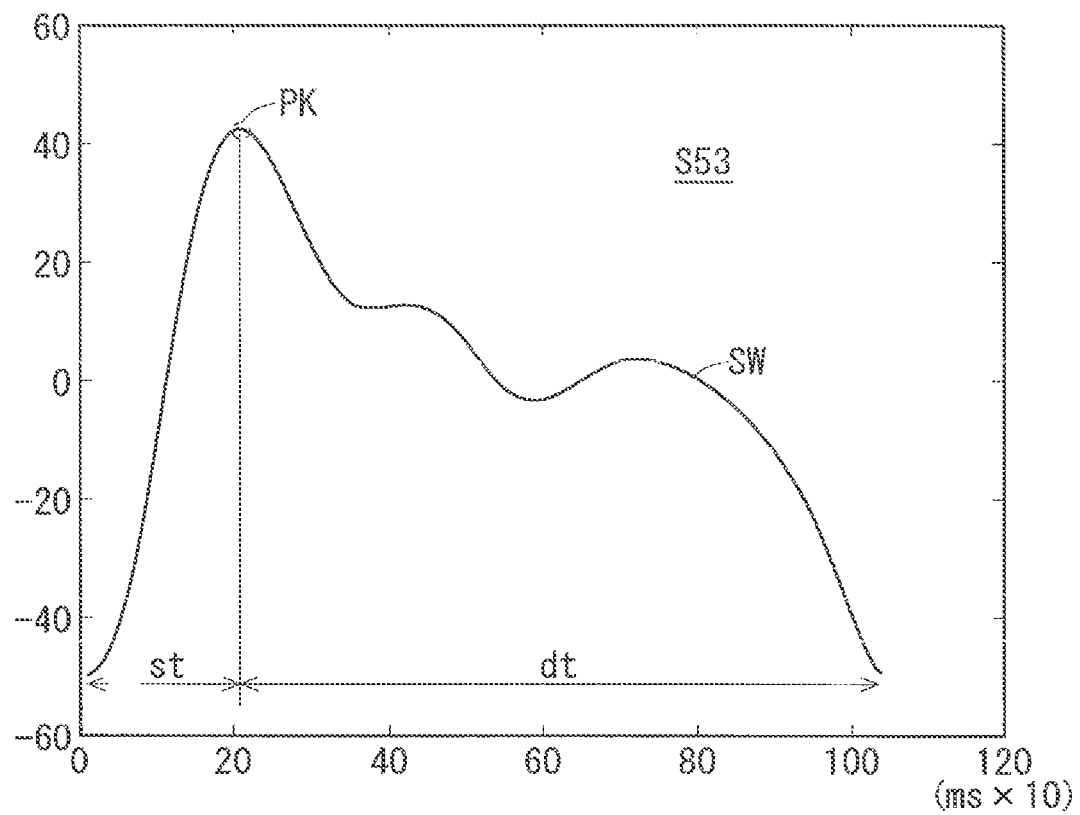
FIG. 5 is a graph showing a waveform of a single pulse signal.

FIG. 5 is a graph showing a waveform of the single pulse signal S53. The horizontal axis of FIG. 5 is indicated in time (ms×10), and the vertical axis of FIG. 5 indicates spectral intensity as in FIGS. 3 and 4.

As shown in FIG. 5, the time information extraction unit 64 calculates, from a single waveform SW of the single pulse signal S53, the up time st, during which the single pulse signal S53 continues to rise toward a positive peak position PK, and the down time dt, during which the single pulse signal S53 continues to fall from the positive peak position PK.

In a case where a variation of up times st and a variation of down times dt are each equal to or smaller than a threshold, and a up and down (mean) time ratio st/dt that is a ratio of a mean value of the up times st to a mean value of the down times dt is within an allowable range, the time information extraction unit 64 determines the single waveform SW as a qualified waveform, and outputs information indicating the up times st and the down times dt of the qualified waveform as the time information CT. The time information CT is output along with peak information JP4 that is the peak information JP2 corresponding to the qualified waveform.

On the other hand, in a case where the variation of the up times st and the variation of the down times dt each exceeds the threshold, or the up and down time ratio st/dt is out of the allowable range, the time information extraction unit 64 determines the single waveform SW as an abnormal waveform, and discards the up times st and the down times dt of the abnormal waveform without outputting the time information CT.

Qualified waveform determination processing performed by the time information extraction unit 64 is specifically described below. The time information extraction unit 64 obtains a plurality of single pulse signals S53 from one unit of the pulse signal S5 obtained from the waveform separation unit 63. In a case where the difference between a maximum vale st_max and a minimum value st_min of the up times st and the difference between a maximum value dt_max and a minimum value dt_min of the down times dt of the plurality of single pulse signals S53 are each equal to or smaller than 20 samples, and a ratio st_mean/dt_mean of a mean value st_mean of the up times st and a mean value dt_mean of the down times dt of the plurality of single pulse signals S53 is smaller than 0.4, the time information extraction unit 64 determines the waveform as the waveform qualified for blood pressure calculation. The time information extraction unit 64 then outputs the time information CT indicating the up times st and the down times dt of the plurality of single pulse signals S53 of the qualified waveform to the pulse and blood pressure operation unit 65 located further downstream than the time information extraction unit 64.

The pulse and blood pressure operation unit 65 applies the blood pressure estimation equation to the time information CT obtained from the time information extraction unit 64 and the parameter information PR obtained from the parameter learning unit 7 to calculate the estimated blood pressure (the maximum blood pressure and the minimum blood pressure), and outputs the blood pressure information BP indicating the estimated blood pressure to the display 9. In this case, the time information CT used to calculate the blood pressure information BP is output to the parameter learning unit 7.

The pulse and blood pressure operation unit 65 further calculates the measured pulse p as necessary based on the mean value of the peak-to-peak distances indicated by the peak information JP4, and outputs the pulse information HR indicating the measured pulse to the parameter learning unit 7. The measured pulse p may be a mean value of pulses calculated from peak-to-peak distances during a certain period of time (e.g., five seconds).

(2-2-1. Blood Pressure Estimation Equation: Operation Model I)

When the estimated blood pressure is represented by bp, a transition time mean value as a mean value stg of the up times st or a mean value dtg of the down times dt is represented by tg, and a first parameter and a second parameter indicated by the parameter information PR are respectively represented by a1 and b1, an operation model I of the blood pressure estimation equation is defined by an equation (a) shown below. The mean value stg and the mean value dtg respectively refer to a mean value of M up times st and a mean value of M down times dt of M single pulse signals S53 extracted from the pulse signal S5 conforming to the pulse signal S4 obtained through buffering by the buffer 4.

$$bp = a1 \cdot tg + b1 \quad (a)$$

The above-mentioned equation (a) is a linear auto-regressive model. In a case where a buffering time of the buffer 4 is five seconds, for example, M is approximately five or six (see FIGS. 3 and 4).

As described above, the equation (a) as the operation model I of the blood pressure estimation equation is set using the parameter a1 (first parameter) that is a coefficient corresponding to the transition time mean value tg as the time information and the parameter b1 (second parameter) that is a constant term.

As described above, the mean value stg of M up times st or the mean value dtg of M down times dt is used as the transition time mean value tg. The estimated blood pressure bp based on the up time mean value stg is maximum blood pressure (a maximum blood pressure value) bpMAX, and the estimated blood pressure bp based on the down time mean value dtg is minimum blood pressure (a minimum blood pressure value) bpMin. This means that the equation (a) is more precisely subdivided into the following equations (as) and (ad):

$$bp\ MAX = a1s \cdot stg + b1s \quad (as)$$

$$bp\ Min = a1d \cdot dtg + b1d \quad (ad)$$

As described above, the parameter a1 as the first parameter is subdivided into a parameter a1s and a parameter a1d, and the parameter b1 as the second parameter is subdivided into a parameter b1s and a parameter b1d.

(2-2-2. Blood Pressure Estimation Equation: Operation Model II)

When the estimated blood pressure is represented by bp, the measured pulse is represented by p, the transition time mean value is represented by tg, and the first parameter, the second parameter, and a third parameter indicated by the parameter information PR are respectively represented by a2, b2, and c2, an operation model II of the blood pressure estimation equation as the linear auto-regressive model is defined by the following equation (b):

$$bp = a2 \cdot tg + b2 \cdot p + c2 \quad (b)$$

The above-mentioned equation (b) is the linear auto-regressive model. As described above, the equation (b) as the operation model II of the blood pressure estimation equation is set using the parameter a2 (first parameter) that is a coefficient corresponding to the transition time mean value tg as the time information, the parameter b2 (second parameter) that is a coefficient corresponding to the measured pulse p as the pulse information, and the parameter c2 (third parameter) that is a constant term.

The estimated blood pressure bp based on the up time mean value stg is maximum blood pressure (a maximum blood pressure value) bpMAX, and the estimated blood pressure bp based on the down time mean value dtg is minimum blood pressure (a minimum blood pressure value) bpMin in the operation model II as in the operation model I. This means that the equation (b) is subdivided into the following equations (bs) and (bd):

$$bp\ MAX = a2s \cdot stg + b2s \cdot p + c2s \quad (bs)$$

$$bp\ MIN = a2d \cdot dtg + b2d \cdot p + c2d \quad (bd)$$

As described above, the parameter a2 as the first parameter is subdivided into a parameter a2s and a parameter a2d, the parameter b2 as the second parameter is subdivided into a parameter b2s and a parameter b2d, and the parameter c2 as the third parameter is subdivided into a parameter c2s and a parameter c2d.

As described above, the pulse and blood pressure operation unit 65 applies the transition time mean value tg (the up time mean value stg and the down time mean value dtg) as the time information CT to the blood pressure estimation equation defined by the equation (a) (the equations (as) and (ad)) or the equation (b) (the equations (bs) and (bd)) to calculate the estimated blood pressure bp (bpMAX and bpMin).

(2-3. Conventional Calibration)

The above-mentioned parameters a1 and b1 and parameters a2 to c2 are important values to derive the estimated blood pressure bp, and a method of determining the parameters is referred to as calibration.

Conventional calibration is described first by taking the equation (a) as the operation model I as an example. In order to obtain accurate parameters a1 and b1, a subject is required to measure blood pressure using an actual sphygmomanometer (a reference sphygmomanometer) other than the blood pressure measurement apparatus of the present invention to obtain reference blood pressure. For example, n transition time mean values tg1 to tgn used by the blood pressure measurement apparatus according to the present embodiment are measured, and n reference blood pressures bp1 to bpn corresponding to the n transition time mean values tg1 to tgn are obtained using the above-mentioned reference sphygmomanometer. As a result, n simultaneous equations can be set up as shown in the following equations (3) (equations (31) to (3n)):

$$\left. \begin{array}{l} bp1 = a1 \cdot tg1 + b1 \ \ldots\ (31) \\ bp2 = a1 \cdot tg2 + b1 \ \ldots\ (32) \\ \phantom{bp2 = a1 \cdot tg2 + b1} \ldots \\ bpn = a1 \cdot tgn + b1 \ \ldots\ (3n) \end{array} \right\} \quad (3)$$

The n transition time mean values tg1 to tgn and the n references bp1 to bpn are substituted in the equations (3), and calculation is performed using a least square (LS) algorithm so that a squared error between the left-hand side (values actually measured by the reference sphygmomanometer) and the right-hand side (estimated blood pressures obtained from the equations (a)) is minimized to eventually determine the parameters a1 and b1.

In conventional calibration, it is necessary to measure blood pressure n times (a few dozen times) in advance to obtain the simultaneous equations (3) using the reference sphygmomanometer other than the blood pressure measurement apparatus according to the present embodiment for each subject. This significantly reduces usability of the blood pressure measurement apparatus that is wearable, and is primarily intended to easily measure blood pressure. Such a problem in conventional calibration can be solved by the parameter learning unit 7 of the blood pressure measurement apparatus according to the present embodiment described below.

(2-4. Parameter Learning Unit)

As shown in FIG. 2C, the parameter learning unit 7 includes a time information accumulation unit 71, a parameter change unit 72, and a time information storage unit 73.

The time information accumulation unit 71 receives the time information CT, and also receives the pulse information HR as necessary from the blood pressure calculation unit 6. This means that the time information accumulation unit 71 receives the pulse information HR in a case where the blood pressure calculation unit 6 obtains the estimated blood pressure using the operation model II defined by the equation (b).

The time information accumulation unit 71 includes therein a register (not shown) for storing K transition times t (up times st and down times dt) required for statistical processing and indicated by the time information CT and K measured pulses p required for statistical processing and indicated by the pulse information HR. K is approximately "30", for example, and is set to have a value much greater than M, which is the number of times used by the blood pressure calculation unit 6 to obtain the transition time mean value tg.

Until K transition times t (up times st or down times dt) and K measured pulses p are stored in the register, K transition times t and K measured pulses p are prepared using the transition times t and the measured pulses p set in advance or the transition times t and the measured pulses p indicated by the time information CT stored in the past in the time information storage unit 73 described later.

When K transition times t and K measured pulses p are prepared, first statistical processing of obtaining a time mean value tm that is a mean value of K transition times t and a time standard deviation σat that is a standard deviation of K transition times t is performed based on K transition times t (a plurality of transition times) as received.

The time information accumulation unit 71 further performs second statistical processing of obtaining a maximum time $t_{max}$ (a time maximum value) that is a maximum value of K transition times t and a minimum time $t_{min}$ (a time minimum value) that is a minimum value of K transition times t as necessary.

In addition, the time information accumulation unit 71 performs third statistical processing of obtaining a pulse mean value pm that is a mean value of K measured pulses p, a pulse standard deviation $\sigma_p$ that is a standard deviation of K measured pulses p, a maximum pulse $p_{max}$ (a pulse maximum value) that is a maximum value of K measured pulses p, and a minimum pulse $p_{min}$ (a pulse minimum value) that is a minimum value of K measured pulses p based on K measured pulses p as necessary.

The time information accumulation unit 71 performs all the above-mentioned first to third statistical processing in a case where the blood pressure calculation unit 6 obtains the estimated blood pressure using the operation model II defined by the equation (b), and performs only the above-mentioned first statistical processing in a case where the blood pressure calculation unit 6 obtains the estimated blood pressure using the operation model I defined by the equation (a).

The information (the time mean value tm, the time standard deviation $\sigma_t$, the maximum time $t_{max}$, and the minimum time $t_{min}$) obtained based on K transition times t corresponds to the statistical time information TJ, and the information (the pulse mean value pm, the pulse standard deviation $\sigma_p$, the maximum pulse $p_{max}$, and the minimum pulse $p_{min}$) obtained based on K measured pulses p corresponds to the statistical pulse information PJ.

Although a case where the number of transition times t used in the first and second statistical processing and the number of measured pulses p used in the third statistical processing are both K is described above, the number of transition times t and the number of measured pulses p used in the statistical processing may be set to have different values.

The time information accumulation unit 71 outputs the time information CT (and the pulse information HR as necessary) and the statistical time information TJ (and the statistical pulse information PJ as necessary) to the parameter change unit 72 located further downstream than the time information accumulation unit 71.

The time information accumulation unit 71 further stores, in another register, the basic blood pressure information JB that is externally received, and outputs the basic blood pressure information JB to the parameter change unit 72 as it stands.

The parameter change unit 72 receives, from the time information accumulation unit 71, the time information CT, the basic blood pressure information JB, and the statistical time information TJ as well as the pulse information HR and the statistical pulse information PJ as necessary, applies the basic blood pressure information JB and the statistical time information TJ (as well as the statistical pulse information PJ as necessary) to the learning operational equation to update the parameters for the blood pressure estimation equation, and outputs the parameter information PR indicating the updated parameters to the pulse and blood pressure operation unit 65 of the blood pressure calculation unit 6.

(2-4-1. Learning Operational Equation: Corresponding to Operation Model I)

The learning operational equation corresponding to the equation (a) as the operation model I is defined by equations (1) shown below. The equations (1) include a combination of equations (11) and (12). In the equations (1), SBP represents reference blood pressure, and δ represents a blood pressure variation range in which the reference blood pressure SBP varies, and the reference blood pressure SBP and the blood pressure variation range δ are indicated by the basic blood pressure information JB.

$$\left. \begin{array}{l} SBP \cdot (1+\delta) = a1 \cdot (tm - \sigma_t) + b1 \ \ldots \ (11) \\ SBP \cdot (1-\delta) = a1 \cdot (tm + \sigma_t) + b1 \ \ldots \ (12) \end{array} \right\} \quad (1)$$

SBP: reference blood pressure
δ: blood pressure variation range
tm: time mean value
$\sigma_t$: standard deviation The up time mean value stm or the down time mean value dtm is specifically used as the time mean value tm, equations (1s) shown below are used to correspond to the parameters a1s and b1s used in the equation (as) as the blood pressure estimation equation, and equations (1d) shown below are used to correspond to the parameters a1d and b1d used in the equation (ad) as the blood pressure estimation equation. This means that the equations (1) are more precisely subdivided into the following equations (1s) and (1d):

$$SBP \cdot (1+\delta) = a1s \cdot (stm - \sigma_t) + b1s \quad \ldots (11s)$$
$$SBP \cdot (1-\delta) = a1s \cdot (stm + \sigma_t) + b1s \quad \ldots (12s)$$
(1s)

stm: up time mean value $$SBP \cdot (1+\delta) = a1d \cdot (dtm - \sigma_t) + b1d \quad \ldots (11d)$$
$$SBP \cdot (1-\delta) = a1d \cdot (dtm + \sigma_t) + b1d \quad \ldots (12d)$$
(1d)

dtm: down time mean value

As described above, the parameter a1 in the equations (1) is subdivided into the parameter a1s in the equations (1s) and the parameter a1d in the equations (1d), and the parameter b1 in the equations (1) is subdivided into the parameter b1s in the equations (1s) and the parameter b1d in the equations (1d).

The parameter change unit 72 performs learning processing of solving the above-mentioned simultaneous equations (1) (equations (1s) and (1d)) to obtain the parameter a1 (parameters a1s and a1d) and the parameter b1 (parameters b1s and b1d), and outputs the parameter information PR indicating the obtained parameters a1 and b1 to the pulse and blood pressure operation unit 65 of the blood pressure calculation unit 6.

(2-4-2. Learning Operational Equation: Corresponding to Operation Model II)

The learning operational equation corresponding to the equation (b) as the operation model II is defined by equations (2) shown below. The equations (2) include a combination of equations (21) to (23).

$$SBP \cdot (1+\delta) = a2 \cdot (tm - \sigma_t) + b2 \cdot (pm + \sigma_p) + c2 \quad \ldots (21)$$
$$SBP \cdot (1-\delta) = a2 \cdot (tm + \sigma_t) + b2 \cdot (pm - \sigma_p) + c2 \quad \ldots (22)$$
$$SBP = a2 \cdot \frac{(t_{max} + t_{min})}{2} + b2 \cdot \frac{(p_{max} + p_{min})}{2} + c2 \quad \ldots (23)$$
(2)

pm: pulse mean value
$\sigma_p$: pulse standard deviation
$t_{max}$: maximum time
$t_{min}$: minimum time
$p_{max}$: maximum pulse
$p_{min}$: minimum pulse As in the learning operational equation corresponding to the operation model I, the up time mean value stm or the down time mean value dtm is specifically used as the time mean value tm, equations (2s) shown below are used to correspond to the parameters a1s to c1s used in the equation (bs) as the blood pressure estimation equation, and equations (2d) shown below are used to correspond to the parameters a1d to c1d used in the equation (bd) as the blood pressure estimation equation in the learning operational equation corresponding to the operation model II. This means that the equations (2) are more precisely subdivided into the following equations (2s) and (2d):

$$SBP \cdot (1+\delta) = a2s \cdot (stm - \sigma_t) + b2s \cdot (pm + \sigma_p) + c2s \quad \ldots (21s)$$
$$SBP \cdot (1-\delta) = a2s \cdot (stm + \sigma_t) + b2s \cdot (pm - \sigma_p) + c2s \quad \ldots (22s)$$
$$SBP = a2s \cdot \frac{(st_{max} + st_{min})}{2} + b2s \cdot \frac{(p_{max} + p_{min})}{2} + c2s \quad \ldots (23s)$$
(2s)

$st_{max}$: up maximum time
$st_{min}$: up minimum time $$SBP \cdot (1+\delta) = a2d \cdot (dtm - \sigma_t) + b2d \cdot (pm + \sigma_p) + c2d \quad \ldots (21d)$$
$$SBP \cdot (1-\delta) = a2d \cdot (dtm + \sigma_t) + b2d \cdot (pm - \sigma_p) + c2d \quad \ldots (22d)$$
$$SBP = a2d \cdot \frac{(dt_{max} + dt_{min})}{2} + b2d \cdot \frac{(p_{max} + p_{min})}{2} + c2d \quad \ldots (23d)$$
(2d)

$dt_{max}$: down maximum time
$dt_{min}$: down minimum time

As described above, the parameter a2 in the equations (2) is subdivided into the parameter a2s in the equations (2s) and the parameter a2d in the equations (2d), the parameter b2 in the equations (2) is subdivided into the parameter b2s in the equations (2s) and the parameter b2d in the equations (2d), and the parameter c2 in the equations (2) is subdivided into the parameter c2s in the equations (2s) and the parameter c2d in the equations (2d).

The parameter change unit 72 performs learning processing of solving the above-mentioned simultaneous equations (2) (equations (2s) and (2d)) to obtain the parameter a2 (parameters a2s and a2d), the parameter b2 (parameters b2s and b2d), and the parameter c2 (parameters c2s and c2d), and outputs the parameter information PR indicating the obtained parameters a2, b2, and c2 to the pulse and blood pressure operation unit 65 of the blood pressure calculation unit 6.

(2-4-3. Time Information Storage Unit)

The time information storage unit 73 stores the time information CT (and the pulse information HR as necessary) obtained from the parameter change unit 72 in flash memory and the like in the time information storage unit 73. The stored information is used in the first to third statistical processing performed by the time information accumulation unit 71 in a case where K transition times t (and K measured pulses p) are not stored in the register.

3. Effects

As described above, the blood pressure calculation unit 6 of the blood pressure measurement apparatus according to the present embodiment can obtain, in calculating the estimated blood pressure by applying the blood pressure estimation equation defined by the equation (a) or (b), accurate estimated blood pressure by using the latest parameter information PR sequentially updated by the parameter learning unit 7. In this case, the parameter learning unit 7 performs learning processing of solving the simultaneous equations (1) or (2) using the basic blood pressure information JB received for the subject, and thus can save the effort to necessitate the subject undergoing actual blood pressure measurement using a sphygmomanometer other than the blood pressure measurement apparatus according to the present embodiment in performing learning processing.

As a result, the blood pressure measurement apparatus according to the present embodiment is easy to use, and can obtain accurate estimated blood pressure.

In a case where the above-mentioned operation model I is used, the blood pressure calculation unit 6 of the blood pressure measurement apparatus according to the present embodiment applies the blood pressure estimation equation defined by the equation (a) to the parameters a1 and b1, which are the first and second parameters, and the time mean value tg, which is the time information, to obtain, in real time, the estimated blood pressure from the time mean value tg calculated based on the photoplethysmography signal S obtained every moment.

In this case, the parameter learning unit 7 performs learning processing of applying the learning operational equation defined by the above-mentioned equations (1) (equations (1s) and (1d)) to the reference blood pressure SBP and the blood pressure variation range δ as well as the time mean value tm and the time standard deviation $\sigma_t$, which are the statistical time information TJ. The parameter learning unit 7 updates the parameters a1 and b1 as appropriate by solving the simultaneous equations (1) to thereby maintain high reliability of the blood pressure estimation equation defined by the equation (a).

In a case where the above-mentioned operation model II is used, the blood pressure calculation unit 6 of the blood pressure measurement apparatus according to the present embodiment applies the blood pressure estimation equation defined by the equation (b) to the parameters a2 to c2, which are the first to third parameters, the time mean value tg, which is the time information, and the measured pulse p, which is the pulse information, to obtain, in real time, the estimated blood pressure from the time mean value tg and the measured pulse p calculated based on the photoplethysmography signal S1 obtained every moment.

In this case, the parameter learning unit 7 performs learning processing of applying the learning operational equation defined by the above-mentioned equations (2) to the reference blood pressure SBP and the blood pressure variation range δ as well as the time mean value tm, the maximum time $t_{max}$ (time maximum value), the minimum time $t_{min}$ (time minimum value), and the time standard deviation $\sigma_t$, which are the statistical time information TJ, and the pulse mean value pm, the maximum pulse $p_{max}$ (pulse maximum value), the minimum pulse $p_{min}$ (pulse minimum value), and the pulse standard deviation $\sigma_p$, which are the statistical pulse information PJ. The parameter learning unit 7 updates the parameters a2 to c2 as appropriate by solving the simultaneous equations (2) to thereby maintain high reliability of the blood pressure estimation equation defined by the equation (b).

In addition, the blood pressure calculation unit 6 according to the present embodiment obtains the maximum blood pressure (value) bpMAX, which is the estimated blood pressure indicating the maximum blood pressure, from the equation (as) or (bs) as a maximum blood pressure estimation equation corresponding to the up time st (rise time).

In this case, the parameter learning unit 7 updates the parameters a1s and b1s or the parameters a2s to c2s, which are the parameters for the maximum blood pressure estimation equation, as appropriate by applying the equations (1s) or (2s) as a maximum blood pressure learning operational equation to thereby maintain high reliability of the maximum blood pressure estimation equation (equation (as) or (bs)).

Furthermore, the blood pressure measurement unit 11 obtains the minimum blood pressure bpMin, which is the estimated blood pressure indicating the minimum blood pressure, from the equation (ad) or (bd) as a minimum blood pressure estimation equation corresponding to the down time dt (fall time).

In this case, the parameter learning unit 7 updates the parameters a1d and b1d or the parameters a2d to c2d, which are the parameters for the minimum blood pressure estimation equation, as appropriate by applying the equations (1d) or (2d) as a minimum blood pressure learning operational equation to thereby maintain high reliability of the minimum blood pressure estimation equation (equation (ad) or (bd)).

4. Others

Although the waveform selection unit 62 of the blood pressure calculation unit 6 shown in FIG. 2B imposes the conditions (1) and (2) as the qualifying standard for pulse measurement, the waveform selection unit 62 may output the pulse signal S5 as the selected pulse signal S52 as it stands without imposing the conditions (1) and (2) in a case where the operation model I (equation (a)) not requiring the measured pulse p is used.

Although the parameter learning unit 7 shown in FIG. 2C is configured so that the basic blood pressure information JB is transferred to the parameter change unit 72 via the time information accumulation unit 71, the basic blood pressure information JB may directly be output to the parameter change unit 72.

Embodiments of the present invention can be modified or omitted as appropriate within the scope of the invention.

While the invention has been described in detail, the foregoing description is in all aspects illustrative and not restrictive. It is therefore understood that numerous modifications can be devised without departing from the scope of the invention.

What is claimed is:

1. A blood pressure measurement apparatus comprising circuitry configured to:
   detect a pulse of a subject to obtain a photoplethysmography signal; and
   obtain estimated blood pressure of said subject based on said photoplethysmography signal, wherein
   the circuitry is configured to
   receive parameter information, generate time information based on said photoplethysmography signal, and apply a blood pressure estimation equation to said time information and said parameter information to calculate said estimated blood pressure, and
   receive basic blood pressure information for said subject and said time information, and perform learning processing of applying a learning operational equation to statistical time information and said basic blood pressure information to update said parameter information, the statistical time information being obtained by performing statistical processing on said time information,
   wherein
   said basic blood pressure information includes reference blood pressure and a blood pressure variation range in which said reference blood pressure varies,
   said time information includes a transition time that is a time during which said photoplethysmography signal transitions in one direction in which said photoplethysmography signal rises or falls,
   said statistical time information includes a time mean value and a time standard deviation, the time mean value being a mean value of a plurality of transition times obtained by receiving said transition time a plurality of times, the time standard deviation being a standard deviation of said plurality of transition times, said parameter information includes a first parameter and a second parameter, said blood pressure estimation equation includes an equation including said first parameter as a coefficient corresponding to said time information and said second parameter as a constant term, and when said reference blood pressure is represented by SBP, said blood pressure variation range is represented by δ, said time mean value is represented by tm, said time standard deviation is represented by $\sigma_t$, said first parameter is represented by a1, and said second parameter is represented by b1, said learning operational equation is defined by the following equations (1):

$$\left. \begin{array}{l} SBP \cdot (1 + \delta) = a1 \cdot (tm - \sigma_t) + b1 \ \ldots \ (11) \\ SBP \cdot (1 - \delta) = a1 \cdot (tm + \sigma_t) + b1 \ \ldots \ (12) \end{array} \right\} \quad (1)$$

2. The blood pressure measurement apparatus according to claim 1, wherein said plurality of transition times include a plurality of rise times during which said photoplethysmography signal transitions in a direction in which said photoplethysmography signal rises, and a plurality of fall times during which said photoplethysmography signal transitions in a direction in which said photoplethysmography signal falls, said blood pressure estimation equation includes a maximum blood pressure estimation equation corresponding to said rise times and a minimum blood pressure estimation equation corresponding to said fall times, and said learning operational equation includes a maximum blood pressure learning operational equation corresponding to said rise times and a minimum blood pressure learning operational equation corresponding to said fall times.

3. A blood pressure measurement apparatus comprising circuitry configured to:

detect a pulse of a subject to obtain a photoplethysmography signal; and obtain estimated blood pressure of said subject based on said photoplethysmography signal, wherein the circuitry is configured to receive parameter information, generate time information based on said photoplethysmography signal, and apply a blood pressure estimation equation to said time information and said parameter information to calculate said estimated blood pressure, and receive basic blood pressure information for said subject and said time information, and perform learning processing of applying a learning operational equation to statistical time information and said basic blood pressure information to update said parameter information, the statistical time information being obtained by performing statistical processing on said time information, wherein the circuitry is configured to measure a pulse of said subject based on said photoplethysmography signal to further calculate a measured pulse, said blood pressure estimation equation is further applied to pulse information based on said measured pulse, the circuitry is configured to perform statistical processing on said pulse information to further obtain statistical pulse information, said basic blood pressure information includes reference blood pressure and a blood pressure variation range in which said reference blood pressure varies, said time information includes a transition time that is a time during which said photoplethysmography signal transitions in one direction in which said photoplethysmography signal rises or falls, said statistical time information includes a time maximum value, a time minimum value, a time mean value, and a time standard deviation, the time maximum value, the time minimum value, and the time mean value respectively being a maximum value, a minimum value, and a mean value of a plurality of transition times obtained by receiving said transition time a plurality of times, the time standard deviation being a standard deviation of said plurality of transition times, said statistical pulse information includes a pulse maximum value, a pulse minimum value, a pulse mean value, and a pulse standard deviation, the pulse maximum value, the pulse minimum value, and the pulse mean value respectively being a maximum value, a minimum value, and a mean value of a plurality of measured pulses obtained by receiving said measured pulse a plurality of times, the pulse standard deviation being a standard deviation of said plurality of measured pulses, said parameter information includes a first parameter, a second parameter, and a third parameter, said blood pressure estimation equation includes an equation including said first parameter as a coefficient corresponding to said time information, said second parameter as a coefficient corresponding to said pulse information, and said third parameter as a constant term, and when said reference blood pressure is represented by SBP, said blood pressure variation range is represented by δ, said time minimum value is represented by $t_{min}$, said time maximum value is represented by $t_{max}$, said time mean value is represented by tm, said time standard deviation is represented by $\sigma_t$, said pulse minimum value is represented by $p_{min}$, said pulse maximum value is represented by $p_{max}$, said pulse mean value is represented by pm, said pulse standard deviation is represented by $\sigma_p$, said first parameter is represented by a2, said second parameter is represented by b2, and said third parameter is represented by c2, said learning operational equation is defined by the following equations (2):

$$\left. \begin{array}{l} SBP \cdot (1 + \delta) = a2 \cdot (tm - \sigma_t) + b2 \cdot (pm + \sigma_p) + c2 \ \ldots \ (21) \\ SBP \cdot (1 - \delta) = a2 \cdot (tm + \sigma_t) + b2 \cdot (pm - \sigma_p) + c2 \ \ldots \ (22) \\ SBP = a2 \cdot \frac{(t_{max} + t_{min})}{2} + b2 \cdot \frac{(p_{max} + p_{min})}{2} + c2 \ \ldots \ (23) \end{array} \right\} \quad (2)$$

4. The blood pressure measurement apparatus according to claim 3, wherein said plurality of transition times include a plurality of rise times during which said photoplethysmography signal transitions in a direction in which said photoplethysmography signal rises, and a plurality of fall times during which said photoplethysmography signal transitions in a direction in which said photoplethysmography signal falls, said blood pressure estimation equation includes a maximum blood pressure estimation equation corresponding to said rise times and a minimum blood pressure estimation equation corresponding to said fall times, and said learning operational equation includes a maximum blood pressure learning operational equation corresponding to said rise times and a minimum blood pressure learning operational equation corresponding to said fall times.

5. A blood pressure measurement method comprising the steps of:
   (a) detecting a pulse of a subject to obtain a photoplethysmography signal; and
   (b) obtaining estimated blood pressure of said subject based on said photoplethysmography signal, wherein said step (b) includes the steps of:
   (b-1) receiving parameter information, generating time information based on said photoplethysmography signal, and applying a blood pressure estimation equation to said time information and said parameter information to calculate said estimated blood pressure; and
   (b-2) receiving basic blood pressure information for said subject and said time information, and performing learning processing of applying a learning operational equation to statistical time information and said basic blood pressure information to update said parameter information, the statistical time information being obtained by performing statistical processing on said time information, wherein said basic blood pressure information includes reference blood pressure and a blood pressure variation range in which said reference blood pressure varies, said time information includes a transition time that is a time during which said photoplethysmography signal transitions in one direction in which said photoplethysmography signal rises or falls, said statistical time information includes a time mean value and a time standard deviation, the time mean value being a mean value of a plurality of transition times obtained by receiving said transition time a plurality of times, the time standard deviation being a standard deviation of said plurality of transition times, said parameter information includes a first parameter and a second parameter, said blood pressure estimation equation includes an equation including said first parameter as a coefficient corresponding to said time information and said second parameter as a constant term, and when said reference blood pressure is represented by SBP, said blood pressure variation range is represented by $\delta$, said time mean value is represented by tm, said time standard deviation is represented by $\sigma_t$, said first parameter is represented by a1, and said second parameter is represented by b1, said learning operational equation is defined by the following equations (1):

$$\left. \begin{array}{l} SBP \cdot (1+\delta) = a1 \cdot (tm - \sigma_t) + b1 \ \ldots \ (11) \\ SBP \cdot (1-\delta) = a1 \cdot (tm + \sigma_t) + b1 \ \ldots \ (12) \end{array} \right\} (1).$$

\* \* \* \* \*